(12) United States Patent
Stinchfield et al.

(10) Patent No.: US 9,427,325 B2
(45) Date of Patent: Aug. 30, 2016

(54) INTERBODY IMPLANT AND METHOD

(71) Applicant: Warsaw Orthopedic, Inc., Warsaw, IN (US)

(72) Inventors: Thomas J. Stinchfield, Memphis, TN (US); Robert M. Loke, Memphis, TN (US); Thomas E. Drochner, Memphis, TN (US); Michael M. Merves, Memphis, TN (US); Julien J. Prevost, Memphis, TN (US); Aubrey R. Mills, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 377 days.

(21) Appl. No.: 13/951,572

(22) Filed: Jul. 26, 2013

(65) Prior Publication Data

US 2015/0032210 A1  Jan. 29, 2015

(51) Int. Cl.
*A61F 2/44* (2006.01)
*A61F 2/30* (2006.01)
*A61F 2/28* (2006.01)

(52) U.S. Cl.
CPC .............. *A61F 2/44* (2013.01); *A61F 2/30744* (2013.01); *A61F 2002/2835* (2013.01); *A61F 2002/305* (2013.01); *A61F 2002/3038* (2013.01); *A61F 2002/3055* (2013.01); *A61F 2002/30153* (2013.01); *A61F 2002/30377* (2013.01); *A61F 2002/30405* (2013.01); *A61F 2002/30495* (2013.01); *A61F 2002/30507* (2013.01); *A61F 2002/30601* (2013.01); *A61F 2002/30841* (2013.01)

(58) Field of Classification Search
CPC .............................. A61F 2/4425; A61F 2/442
See application file for complete search history.

(56) References Cited

U.S. PATENT DOCUMENTS

| | | | | |
|---|---|---|---|---|
| 5,674,294 A * | 10/1997 | Bainville | ................ | A61F 2/442 623/17.16 |
| 5,683,394 A * | 11/1997 | Rinner | .................. | A61F 2/4455 606/247 |
| 5,888,223 A * | 3/1999 | Bray, Jr. | ................. | A61F 2/442 606/247 |
| 6,102,950 A * | 8/2000 | Vaccaro | .................. | A61F 2/447 606/247 |
| 6,296,664 B1 * | 10/2001 | Middleton | .......... | A61F 2/30744 623/17.13 |
| 6,447,543 B1 * | 9/2002 | Studer | ................... | A61F 2/2846 623/17.11 |
| 6,641,614 B1 * | 11/2003 | Wagner | ................. | A61F 2/4455 623/17.15 |
| 6,730,088 B2 | 5/2004 | Yeh | | |
| 8,211,178 B2 * | 7/2012 | Melkent | .................... | A61F 2/44 623/17.16 |
| 2002/0143399 A1 * | 10/2002 | Sutcliffe | ................... | A61F 2/44 623/17.11 |
| 2003/0040802 A1 * | 2/2003 | Errico | ..................... | A61F 2/442 623/17.14 |
| 2003/0176923 A1 * | 9/2003 | Keller | ................... | A61F 2/4425 623/17.14 |
| 2003/0181980 A1 * | 9/2003 | Berry | .................... | A61F 2/4455 623/17.11 |

(Continued)

OTHER PUBLICATIONS

VLIFT Vertebral Body Replacement System.

*Primary Examiner* — Christian Sevilla

(57) ABSTRACT

An interbody endcap includes a wall having a first surface connected to an interbody implant and a second surface including an arcuate portion configured for engagement with a vertebral endplate surface. The second surface extends outwardly from the interbody implant to at least adjacent a perimeter of the vertebral endplate surface. Systems and methods are disclosed.

20 Claims, 14 Drawing Sheets

(56) References Cited

U.S. PATENT DOCUMENTS

| | | | |
|---|---|---|---|
| 2004/0186569 A1* | 9/2004 | Berry | A61F 2/44 623/17.11 |
| 2004/0210312 A1* | 10/2004 | Neumann | A61F 2/44 623/17.11 |
| 2005/0165485 A1* | 7/2005 | Trieu | A61F 2/4425 623/17.13 |
| 2005/0209697 A1* | 9/2005 | Paponneau | A61F 2/44 623/17.15 |
| 2005/0273172 A1* | 12/2005 | Patil | A61F 2/442 623/17.16 |
| 2005/0273178 A1* | 12/2005 | Boyan | A61F 2/442 623/23.74 |
| 2006/0111783 A1* | 5/2006 | Aflatoon | A61F 2/4425 623/17.14 |
| 2006/0149378 A1* | 7/2006 | Chase | A61F 2/4425 623/17.11 |
| 2006/0241770 A1* | 10/2006 | Rhoda | A61F 2/44 623/17.15 |
| 2007/0191954 A1 | 8/2007 | Hansell et al. | |
| 2008/0221690 A1* | 9/2008 | Chaput | A61B 17/686 623/17.16 |
| 2008/0306599 A1* | 12/2008 | Morrison, III | A61F 2/4455 623/17.16 |
| 2008/0319548 A1* | 12/2008 | Kuras | A61F 2/442 623/17.11 |
| 2009/0164017 A1* | 6/2009 | Sommerich | A61F 2/4611 623/17.16 |
| 2010/0094424 A1 | 4/2010 | Woodburn et al. | |
| 2010/0125334 A1* | 5/2010 | Krueger | A61F 2/442 623/17.16 |
| 2010/0179655 A1* | 7/2010 | Hansell | A61F 2/44 623/17.11 |
| 2010/0191333 A1* | 7/2010 | Morrison, III | A61F 2/44 623/17.11 |
| 2010/0292794 A1* | 11/2010 | Metz-Stavenhagen | A61F 2/44 623/17.11 |
| 2010/0324686 A1* | 12/2010 | Gerner | A61F 2/44 623/17.16 |
| 2011/0098820 A1 | 4/2011 | Blackwell et al. | |
| 2011/0106258 A1 | 5/2011 | Blackwell et al. | |
| 2011/0184523 A1* | 7/2011 | Blackwell | A61F 2/4455 623/17.16 |
| 2011/2184523 | 7/2011 | Blackwell | |
| 2011/0190890 A1* | 8/2011 | Blackwell | A61F 2/30734 623/17.16 |
| 2012/0016476 A1* | 1/2012 | Wilfong | A61F 2/44 623/17.11 |
| 2012/0016478 A1* | 1/2012 | Wilfong | A61F 2/44 623/17.16 |
| 2012/0029634 A1* | 2/2012 | Drochner | A61F 2/4455 623/17.11 |
| 2012/0029640 A1* | 2/2012 | Capote | A61F 2/44 623/17.16 |
| 2012/0089227 A1 | 4/2012 | Jarzem | |
| 2012/0109307 A1* | 5/2012 | Drochner | A61F 2/4455 623/17.16 |
| 2012/0130493 A1* | 5/2012 | McLaughlin | A61F 2/4455 623/17.16 |
| 2012/0150298 A1* | 6/2012 | Bennett | A61F 2/4425 623/17.11 |
| 2012/0209384 A1 | 8/2012 | Arnold | |
| 2012/0239147 A1 | 9/2012 | Winkler | |
| 2012/0277878 A1 | 11/2012 | Sommeruch et al. | |

* cited by examiner

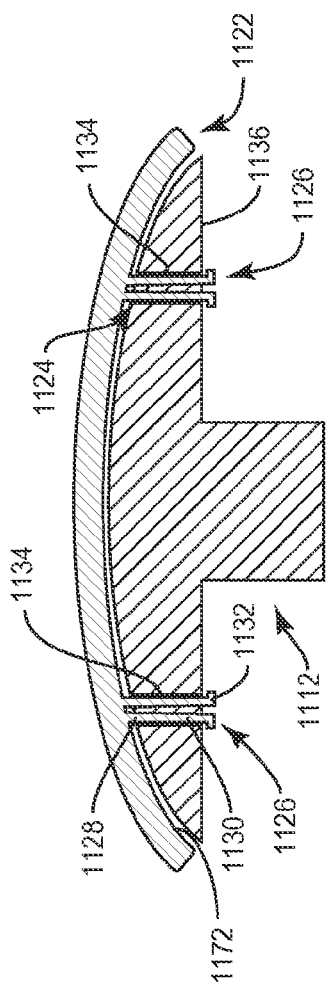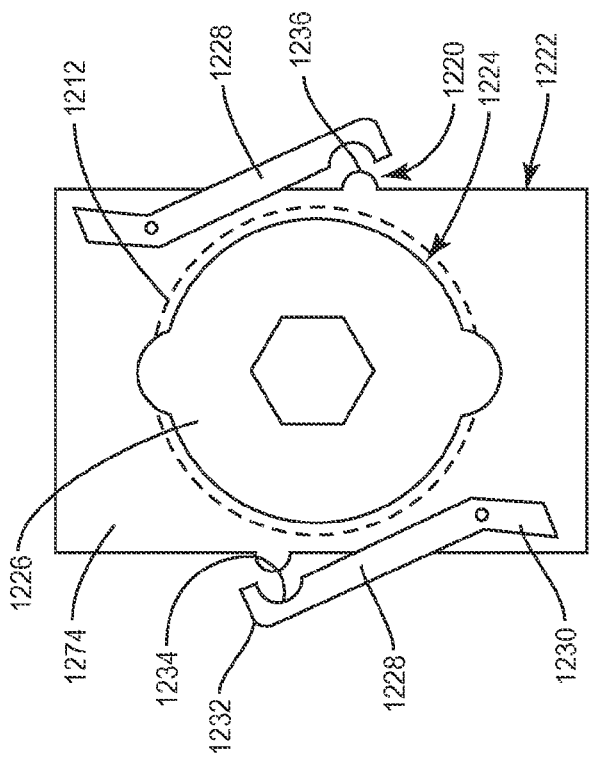

INTERBODY IMPLANT AND METHOD

TECHNICAL FIELD

The present disclosure generally relates to medical devices for the treatment of musculoskeletal disorders, and more particularly to a surgical system that includes an interbody implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae. This disclosure describes an improvement over these prior art technologies.

SUMMARY

In one embodiment, an interbody endcap is disclosed. The interbody endcap includes a wall having a first surface connected to an interbody implant and a second surface including an arcuate portion configured for engagement with a vertebral endplate surface. The second surface extends outwardly from the interbody implant to at least adjacent a perimeter of the vertebral endplate surface. In some embodiments, systems and methods are disclosed.

In one embodiment, the interbody endcap includes a wall having a first surface including a first mating part disposed for engagement with a second mating part of an interbody implant such that the first surface is aligned with the interbody implant such that the wall is disposable in an interlocking configuration with the interbody implant. At least one of the mating parts includes a relatively movable member that is engageable with the other of the mating parts to dispose the wall and the interbody implant in the interlocking configuration. The wall further has a second surface configured for engagement with a vertebral endplate surface.

BRIEF DESCRIPTION OF THE DRAWINGS

The present disclosure will become more readily apparent from the specific description accompanied by the following drawings, in which:

FIG. 17 is a side, cross sectional view of components of one embodiment of a spinal implant in accordance with the principles of the present disclosure;

FIG. 18 is a top view, in part phantom, of components of one embodiment of a spinal implant in accordance with the principles of the present disclosure;

DETAILED DESCRIPTION

Figure 1:
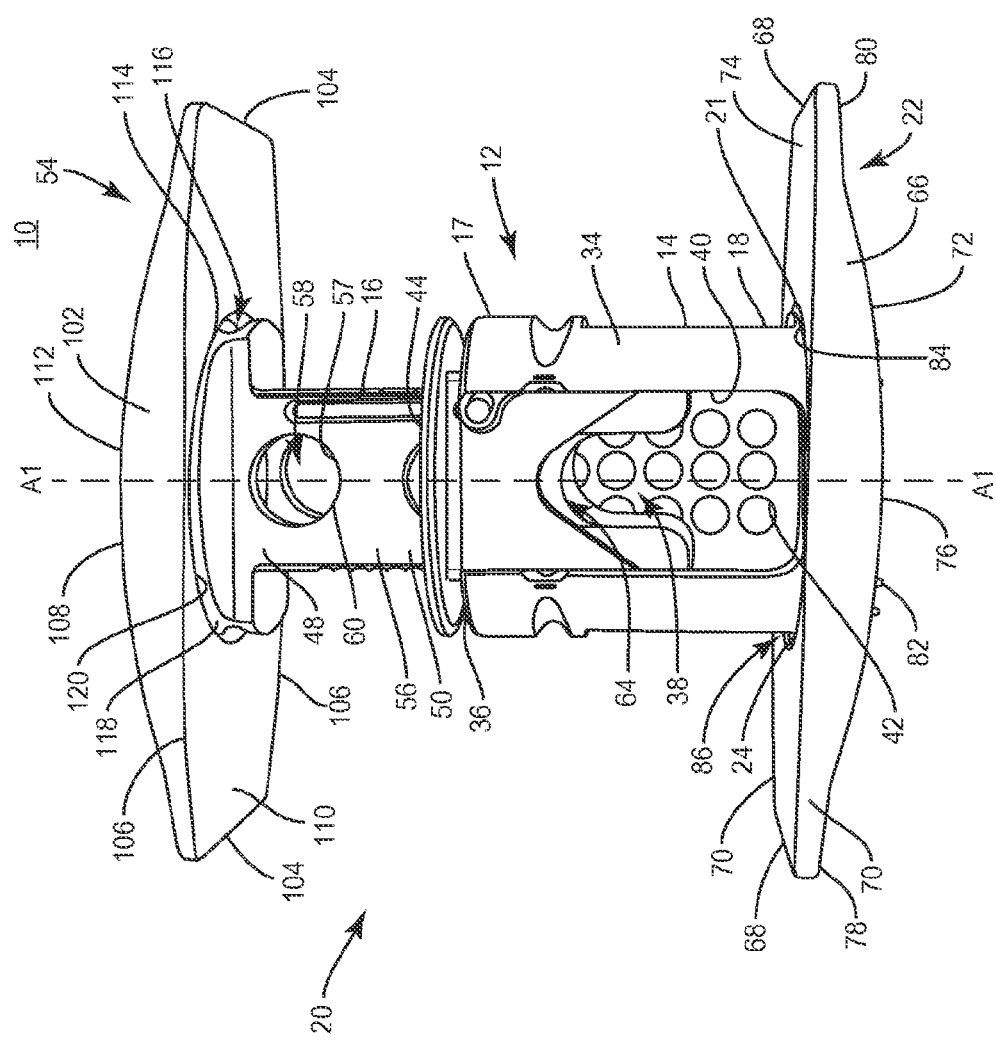
FIG. 1 is a perspective view of components of one embodiment of a spinal implant in accordance with the principles of the present disclosure.

The exemplary embodiments of the surgical system and related methods of use disclosed are discussed in terms of medical devices for the treatment of musculoskeletal disorders and more particularly, in terms of a surgical system that includes an interbody implant and a method for treating a spine.

In one embodiment, the surgical system includes a corpectomy or vertebral body replacement (VBR) implant having extended or widened endcaps and various connection mechanisms for connecting the widened endcaps to either static or expandable implants. In one embodiment, the implant is configured for disposal in a defect in an intervertebral space. In one embodiment, the endcaps are extended and contoured for nested engagement with concave endplates of vertebral bodies. In one embodiment, the endcaps extend out from the center of the defect to the apophyseal ring of a vertebral endplate surface. A majority of the force transferred from the vertebral endplate surfaces to the implant will transfer to the edges of the endcap, which will be in contact with the apophyseal ring or cortical rim of the annulus fibrosis. In one embodiment, a stronger connection between the endcaps and the implant or centerpiece is provided to resist a moment imparted during lateral or sagittal bending of the vertebrae. The various connection mechanisms provided may also be useful for connecting non-extended or non-widened endcaps that have a diameter, length and/or width that approximates a corresponding diameter, length and/or width of the static or expandable implant to which they are attached.

In one embodiment, the endcaps will have a specific length-to-width aspect ratio so as to span the endplates of the vertebral bodies. In one set of exemplary embodiments, the length-to-width aspect ratio of the endcaps will range from 1.1-1 to 1.8-1. In other embodiments the length-to-width aspect ratio of the endcaps may have a greater range from 1-1 to 3-1. In such embodiments, the length of the endcaps may be in a range from 20 mm to 50 mm. In one embodiment, the endcap outer surfaces will have a convex shape. In one embodiment, the endcaps will be connected to the implant centerpiece via a rotate and lock connection mechanism. In one embodiment, the endcaps will be fixed to existing endcaps that are fixed to the expandable or static implant. In one embodiment, the endcaps will be attached to existing endcaps that are articulatingly connected to the expandable or static implant. In one embodiment, the implant is an expandable cage. In one embodiment, the endcap can be connected to an outer body of the implant or a fixed or articulating endcap already connected to a movable inner body of the implant.

In one embodiment, implant end surfaces each include approximately 8 posts extending therefrom configured for mating engagement with spring fingers of endcaps. In one embodiment, a tab of each spring finger is in nested engagement with an undercut or slot of each post. In one embodiment, approximately two spring fingers of an endcap fits into slots defined in pegs extending from end surfaces of an implant. In one embodiment, the spring fingers are wire cut forming a finger of approximately 0.6 millimeters (mm). In one embodiment, a rotate and lock connection is provided. In one embodiment, an endcap is locked to an implant via rotating the endcap into slots defined in approximately 8 pegs extending from a centerpiece of an implant.

In one embodiment, the implant includes a threaded hole located between circumferentially disposed spikes. The endcap also includes a hole through which a set screw is used to connect the endplate to the implant. An underside of the endcap includes indentations corresponding to each spike extending from the implant. The spikes and/or set screws counteract torsion.

In one embodiment, the implant includes a hexagonal hole therethrough. A stem of the endcap includes a correspondingly shaped hex shape fitted with the implant so as to allow for multiple rotational positions to be chosen. The hex geometry resists torsional forces. In one embodiment, the stem of the endcap includes a pair of fingers defining a keyhole shaped recess that allows the fingers to flex and matingly engage a correspondingly-shaped connecting feature in the implant. In one embodiment, flexible wires, such as, for example, Nitinol wires are embedded into the implant and capture an engaging feature disposed at a bottom end of the stem of the endcap.

In one embodiment, the stem of the endcap is similar to a quick connect hose fitting. In one embodiment, splines are disposed on an outer surface of the implant and an underside of the endcap. The splines resist relative rotation of the implant and endcap. Snap fingers and/or set screws maintain contact between the two splined surfaces. In one embodiment, the splines extend down a bone graft hole into a core of the implant. Ridges on the stem of the endcap allow for a plurality of rotational positions and to counteract torsion.

In one embodiment, the endcap includes a separate connecting/locking component. A set screw is threaded through the endcap locking the endcap to the implant. In one embodiment, a snap ring captures the set screw. In one embodiment, the underside of the endcap includes indentations, depressions or through holes to mate with spikes extending from the implant to counteract torsion. In one embodiment, a lower portion of the connecting component includes a cog-like shape. The cog-shaped component matingly engages with a correspondingly shaped hole in the implant. When rotated, the teeth of the cog can engage a series of undercuts to hold the endcap onto the implant. In one embodiment, the endcap includes an external ring that is independently rotatable relative to the implant and the endcap. The ring threadably engages the implant and includes a projection or flange affixed to the endcap whereby connecting the endcap and implant.

In one embodiment, the implant includes a first endcap fixed to the implant. This endcap includes a series of through holes circumferentially disposed. An underside of a second endcap includes one or more features that protrude downward that are configured for engagement with the through holes of the first endcap. Each of the connecting features includes fingers defining a keyhole-shaped recess that matingly engage with the first endcap. In one embodiment, a rotatable central cam is disposed on the endcap. The cam engages one or multiple pivotable arms. When the cam engages the pivotable arms, the arms are forced into a locked position to interface with features extending from the implant. The interface includes, for example, undercuts, recesses, protrusions, or friction fits. The endcap may include through holes or recesses on its underside to correspond to spikes extending from the implant. In one embodiment, the implant includes only one endcap. In one embodiment, the implant includes one or more endcaps that extend uni-laterally from a central body portion of the implant, such as, for example, a cage. For example, only one side of the endcap is extended and can be employed with a partial corpectomy.

In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-5, there is illustrated components of a surgical system, such as, for example, a spinal implant system 10 in accordance with the principles of the present disclosure.

The components of spinal implant system 10 can be fabricated from biologically acceptable materials suitable for medical applications, including metals, synthetic polymers, ceramics and bone material and/or their composites, depending on the particular application and/or preference of a medical practitioner. For example, the components of spinal implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, system 10 may be employed with surgical procedures, such as, for example, corpectomy and discectomy, which include fusion and/or fixation treatments that employ implants, in accordance with the principles of the present disclosure, to restore the mechanical support function of vertebrae.

System 10 includes an implant, such as, for example, a spinal implant 20. Spinal implant 20 includes an interbody implant, such as, for example, a corpectomy cage 12 having a member, such as, for example, an outer body 14 and an inner body 16. Body 14 has a tubular configuration. Body 14 is substantially cylindrical and extends between an end 17 and an end 18 and defines a longitudinal axis A1 therebetween. End 17 defines a substantially planar surface. End 18 defines a substantially planar surface including a mating part 21. In one embodiment, mating part 21 includes a relatively movable member that is engageable with a mating part 24 of an endcap 22, to be described below.

Mating part 21 includes a plurality of circumferentially disposed fixation elements, such as, for example, pegs 26 configured to matingly engage mating part 24 of endcap 22. Pegs 26 extend between a base portion 28 and a cone-shaped portion 30. Each base portion 28 includes a slot 32 oriented radially inward towards axis A1. Slots 32 are configured for disposal of mating part 24 of endcap 22. In some embodiments, end 17 and/or end 18 can include a surface that may be rough, textured, porous, semi-porous, dimpled and/or polished. In some embodiments, portion 30 is variously configured, such as, for example, oval, oblong, triangular, square, hexagonal, polygonal, irregular, uniform, non-uniform and/or tapered.

Body 14 includes a tubular wall 34 that includes an inner surface 36. Surface 36 defines an axial cavity 38 extending between ends 17, 18. In some embodiments, wall 34 defines a cylindrical cross-section of cavity 38. In some embodiments, the cross-section geometry of cavity 38 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 36 is smooth or even. In some embodiments, surface 36 may be rough, textured, porous, semi-porous, dimpled and/or polished.

Wall 34 defines a lateral opening 40 that communicates with cavity 38. Opening 40 is configured to provide access to cavity 38. In one embodiment, opening 40 facilitates delivery and/or introduction of an agent and/or an implant, such as, for example, bone graft and/or other materials into cavity 38. In some embodiments, opening 40 may have various configurations, such as, for example, circular, oval, oblong, triangular, rectangular, polygonal, planar side(s), arcuate side(s), irregular, uniform, non-uniform, offset, staggered, variable, U-shape, kidney bean shape and/or multiple openings.

Wall 34 defines openings 42 configured to facilitate delivery and/or introduction of an agent, bone graft and/or other materials into cavity 38, for employment in a fixation or fusion treatment used for example, in connection with a corpectomy. In one embodiment, the agent may include therapeutic polynucleotides or polypeptides and bone growth promoting material, which can be packed or otherwise disposed on or about the surfaces of the components of spinal implant system 10, including cage 12. The agent may also include biologically active agents, for example, biologically active agents coated onto the exterior and/or interior of cage 12 and/or applied thereto for gradual release such as by blending in a bioresorbable polymer that releases the biologically active agent or agents in an appropriate time dependent fashion as the polymer degrades within the patient. Suitable biologically active agents include, for example, BMP and cytokines. In some embodiments, openings 42 may have various configurations, such as, for example, those described herein.

Figure 2:
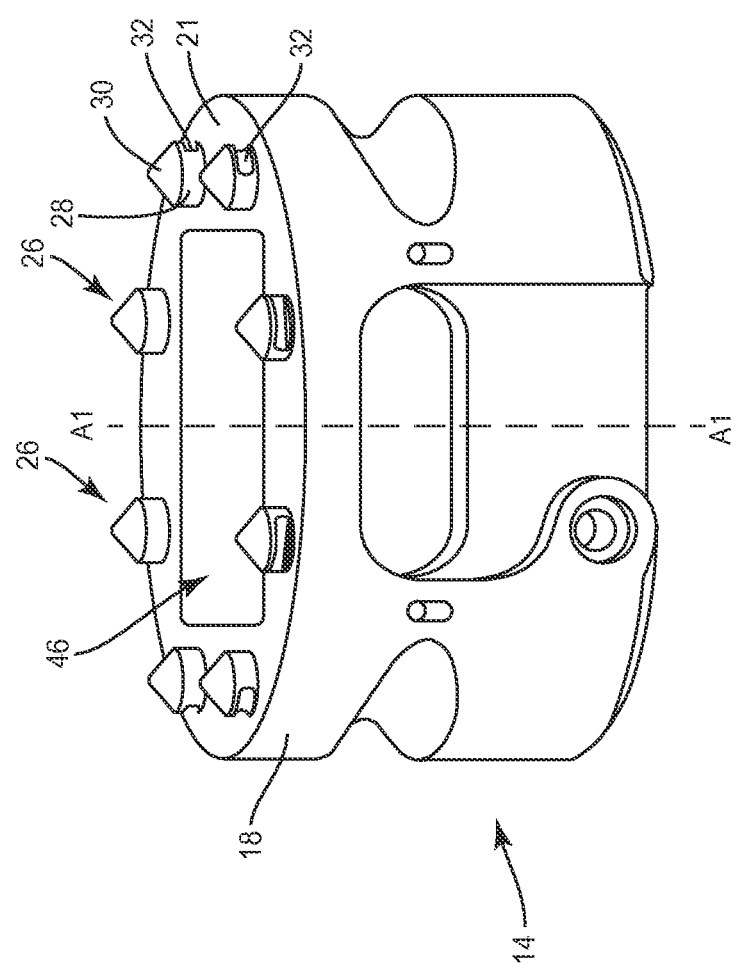
FIG. 2 is a breakaway view of components of the implant shown in FIG. 1.

The planar surface of end 17 defines an opening 44 that communicates with cavity 38. Opening 44 has a rectangular configuration and is configured to provide access to cavity 38. Opening 44 facilitates disposal of a member, such as, for example, inner body 16 with cavity 38, as described herein. The planar surface of end 18 defines an opening 46, as shown in FIG. 2, which communicates with cavity 38. Opening 46 has a rectangular configuration and is configured to provide access to cavity 38. In some embodiments, opening 44 and/or opening 46 may have various configurations, such as, for example, those described herein.

Body 16 has a tubular configuration. Body 16 is substantially rectangular and extends between an end 48 and an end 50 and extends along longitudinal axis A1. End 48 defines a substantially planar surface including a mating part 118, similar to mating part 21 described above with regard to body 14. In one embodiment, mating part 118 includes a relatively movable member (not shown) that is engageable with a mating part 120 of an endcap 54, to be described below. In some embodiments, end 48 can include a surface that may be rough, textured, porous, semi-porous, dimpled and/or polished such that it facilitates engagement with endcap 54. In other embodiments, body 16 may have a variety of alternative cross-sectional configurations including, but not limited to: round; oval; "U" or "C" shaped; and combinations thereof.

Body 16 includes a tubular wall 56. Wall 56 includes an inner surface 57 that defines an axial cavity 58 extending between ends 48, 50. In some embodiments, wall 56 defines a rectangular cross-section of cavity 58. In some embodiments, the cross-section geometry of cavity 58 may have various configurations, such as, for example, those described herein. In some embodiments, inner surface 57 is smooth or even. In some embodiments, inner surface 57 may be rough, textured, porous, semi-porous, dimpled and/or polished.

Wall 56 defines lateral openings 60 that communicate with cavity 58. Openings 60 are configured to provide access to cavity 58. In one embodiment, openings 60 facilitate delivery and/or introduction of an agent into cavity 58. In some embodiments, openings 60 may have various configurations, such as, for example, those alternatives described herein.

The planar surface of end 48 defines an opening (not shown) that communicates with cavity 58. The opening has a circular configuration and is configured to provide access to cavity 58. In one embodiment, the opening facilitates delivery and/or introduction of an agent and/or an implant, such as, for example, bone graft and/or other materials with cavity 58. The planar surface of end 50 defines an opening 64 that communicates with cavity 38 and cavity 58. Opening 64 has a rectangular configuration and is configured to provide access to cavity 38 and cavity 58. In some embodiments, opening 64 may have various configurations, such as, for example, those described herein.

Implant 20 further includes an interbody endcap 22 connected to end 18 of body 14. Endcap 22 includes a wall 66 having a rectangular configuration. In some embodiments, wall 66 has various configurations, such as, for example, oval-shaped, arcuate, crescent, horseshoe, hook-shaped and/or those alternatives described herein. Wall 66 includes a pair of short sides 68 and a pair of long sides 70. Short sides 68 extend to at least a perimeter, such as, for example, an apophyseal ring AR of a vertebral endplate surface E1 of a vertebral body V1. In some embodiments, short sides 68 and/or long sides 70 could be tapered, sloped, angled, or curved, including convex, bi-convex and concave.

Wall 66 has a surface 72 and a surface 74. Wall 66 has a non-uniform thickness defined between surfaces 72, 74. Surface 72 extends outwardly from cage 12 to at least adjacent apophyseal ring AR of vertebral endplate surface E1. Surface 72 includes an arcuate portion 76 configured for engagement with vertebral endplate surface E1 of vertebral body V1. Arcuate portion 76 is disposed in a nested engagement with vertebral endplate surface E1. Surface 72 extends between an end 78 and an end 80 such that arcuate portion 76 is disposed between ends 78, 80. Ends 78, 80 each include a substantially planar configuration oriented transverse to axis A1. Surface 72 is sized and dimensioned such that ends 78, 80 are disposed adjacent opposing ends of apophyseal ring AR or cortical rim of vertebral endplate surface E1. In one embodiment, surface 72 is sized and dimensioned such that only one of ends 78, 80 is disposed adjacent an end of apophyseal ring AR. Surface 72 includes a plurality of fixation elements, such as, for example, spikes 82 configured to engage vertebral tissue. In some embodiments, surface 72 can include a surface that may be rough, textured, porous, semi-porous, dimpled and/or polished such that it facilitates engagement with vertebral tissue, such as, for example, vertebral endplate surface E1. In some embodiments, surface 72 can include an opening corresponding to the size and cross-section geometry of body 14 to deliver an agent, such as, for example, bone graft to vertebral endplate surface E1. In some embodiments, the vertebral tissue may include intervertebral tissue, endplate surfaces and/or cortical bone.

In one embodiment, endcap 22 extends uni-laterally from body 14 such that only one side of endcap 22 is extended and can be employed, for example, with a partial corpectomy. Surface 72 is sized and dimensioned such that one of ends 78, 80 extends outwardly from arcuate portion 76. The uni-laterally extended endcap 22 can be used in a partial corpectomy where vertebral tissue on a lateral side of a vertebral body has been removed and vertebral tissue on the contralateral side of the vertebral body remains intact such that one of ends 78, 80 is disposed in contact with apophyseal ring AR on the lateral side and the other one of ends 78, 80 is disposed with the vertebral tissue on the contralateral side.

Surface 74 or underside of endcap 22 is connected to cage 12. Surface 74 has a substantially planar configuration. In some embodiments, surface 74 can include a surface that may be rough, textured, porous, semi-porous, dimpled and/or polished such that it facilitates engagement with cage 12. Surface 74 includes an inner surface 84 defining a cavity 86 configured for disposal of end 18 of body 14. Cavity 86 has a circular configuration. In some embodiments, cavity 86 is variously shaped, such as, for example, oval, oblong, triangular, rectangular, square, polygonal, irregular, uniform, non-uniform, variable and/or tapered to correspond to variously shaped ends 18 of body 14.

Figure 4:
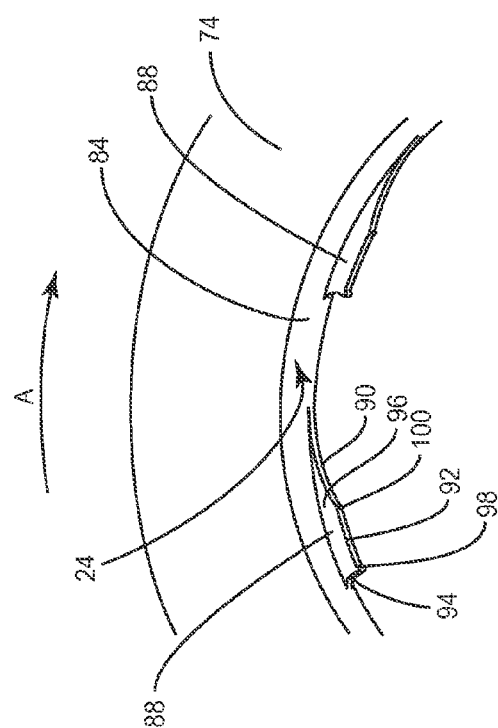
FIG. 4 is an expanded breakaway view of the components shown in FIG. 3.
Figure 3:
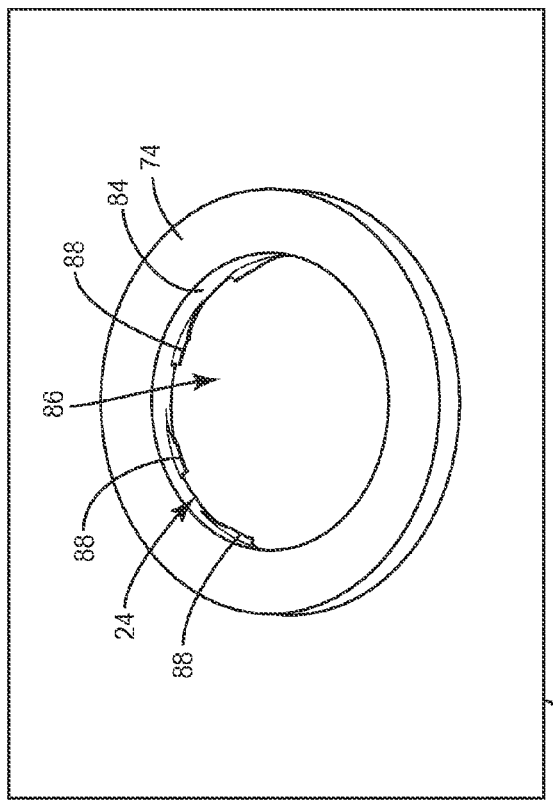
FIG. 3 is a bottom view of components of the implant shown in FIG. 1.

Surface 74 includes mating part 24, as shown in FIGS. 3-4, engaged to mating part 21 of cage 12. Mating part 24 is disposed for engagement with mating part 21 of cage 12 such that surface 74 is aligned with cage 12 such that wall 66 is disposable in an interlocking configuration with cage 12. Surface 74 is connected to cage 12 via rotational interlock of mating parts 21, 24. Mating part 24 includes a relatively movable member that is engageable with mating part 21 of body 14 of cage 12 to dispose wall 66 and cage 12 in the interlocking configuration. The movable member includes a plurality resiliently biased members 88 that are rotatably aligned with corresponding slots 32 of mating part 21 of cage 12 for disposal of wall 66 and cage 12 in the interlocking configuration. Members 88 extend radially inward from inner circular surface 84 of endcap 22. Members 88 include a first portion 90 having a ramped configuration and a second portion 92. Portion 92 extends between an end 94 having a protrusion, such as, for example, a spike 98 and an end 96 having a protrusion, such as, for example, a spike 100. To connect endcap 22 with end 18 of body 14, endcap 22 is rotated, in a direction shown by arrow A in FIG. 4, such that portion 90 engages peg 26 and at least one of member 88 and peg 26 deflect such that portion 92 and slot 32 are rotatably aligned. Peg 26 is captured between spikes 98, 100 to dispose wall 66 and cage 12 in the interlocking configuration.

Implant 20 includes an interbody endcap 54, similar to endcap 22 described above. Endcap 54 is connected to end 48 of body 16 via a similar mating engagement as described above with regard to endcap 22 and end 18 of body 14. Endcap 54 includes a wall 102 having a rectangular configuration. Wall 102 includes a pair of short sides 104 and a pair of long sides 106. Short sides 104 extend to at least a perimeter, such as, for example, an apophyseal ring AR of a vertebral endplate surface E2 of a vertebral body V2. Wall 102 has a surface 108 and a surface 110. Surface 108 extends outwardly from cage 12 to at least adjacent apophyseal ring AR of vertebral endplate surface E2 of vertebral body V2. Surface 108 includes an arcuate portion 112 configured for engagement with vertebral endplate surface E2 of vertebral body V2. Arcuate portion 112 is disposed in a nested engagement with vertebral endplate surface E2.

Surface 110 or underside of endcap 54 is connected to end 48 of body 16. Surface 110 includes an inner surface 114 defining a cavity 116 configured for disposal of end 48 of body 16. Cavity 116 has a circular configuration. Surface 110 includes mating part 120, similar to mating part 24 described above, engaged to mating part 118 of cage 12, similar to mating part 24 described above. Mating part 120 is disposed for engagement with mating part 118 of cage 12 such that surface 110 is aligned with cage 12 such that wall 102 is disposable in an interlocking configuration with cage 12. Surface 110 is connected to cage 12 via rotational interlock of mating parts 118, 120. In some embodiments, endcaps 22, 54 are connected to opposite ends 18, 48, respectively, of cage 12 via welding.

Figure 5:
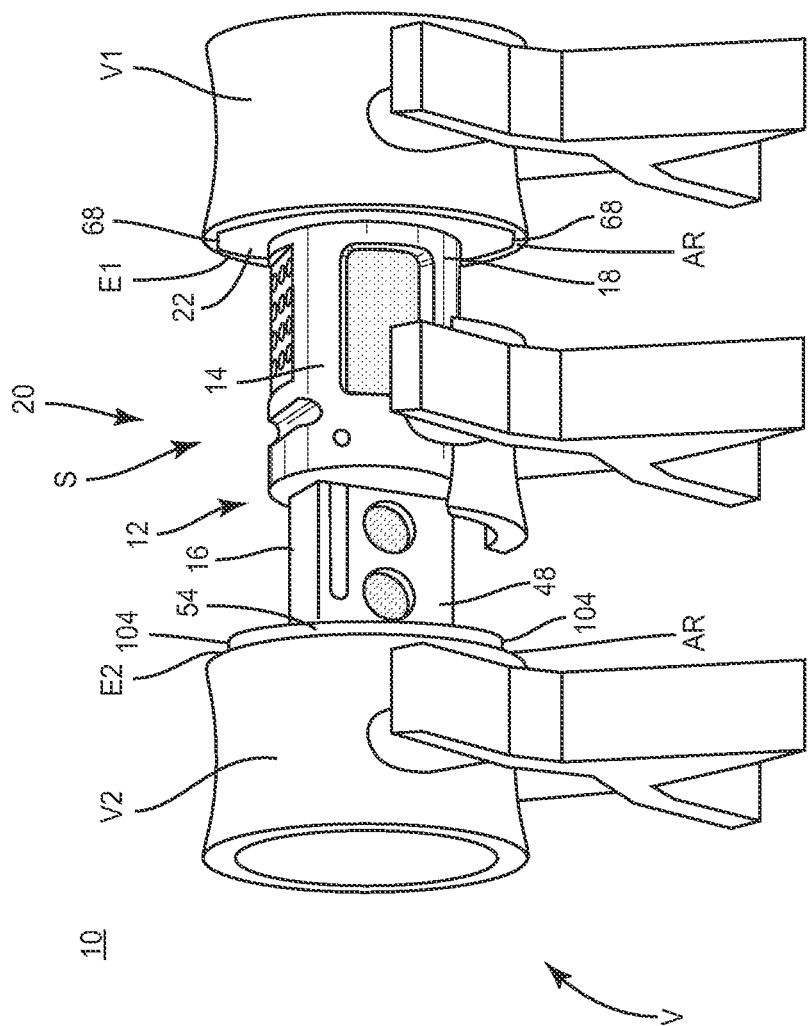
FIG. 5 is a perspective view of components of one embodiment of a spinal implant in accordance with the principles of the present disclosure disposed with vertebrae.

Cage 12 is selectively movable between a first, collapsed and/or nested configuration (not shown) and a second, expanded configuration, as shown, for example, in FIGS. 1 and 5, to restore vertebral spacing and provide distraction and/or restore mechanical support function of vertebrae. In some embodiments, opening 44 facilitates axial translation of body 16 relative to body 14 for selective expansion and/or contraction of bodies 14, 16 between a collapsed and/or nested configuration and an expanded configuration. In some embodiments, cage 12 is disposed in a collapsed, telescopic configuration for delivery and implantation adjacent a surgical site and bodies 14, 16 are expanded in vivo. In some embodiments, cage 12 can be expanded prior to implantation adjacent a surgical site. In some embodiments, cage 12 can be disposed to engage adjacent vertebral soft tissue and bone surfaces to restore height and provide support in place of removed vertebrae and/or intervertebral tissue.

In one embodiment, expansion and/or contraction of cage 12 is facilitated by engagement of respective helical gear surfaces of bodies 14, 16 such that relative rotation of bodies 14, 16 causes axial translation of body 16 relative to body 14. In one embodiment, expansion and/or contraction of cage 12 is facilitated by engagement of a tool with one of bodies 14, 16 to cause axial translation of body 16 relative to body 14. In one embodiment, expansion and/or contraction of cage 12 is facilitated by free hand manipulation of bodies 14, 16 to cause axial translation of body 16 relative to body 14. In one embodiment, expansion and/or contraction of cage 12 is facilitated by engagement of respective pinion gear and rack surfaces of bodies 14, 16 to cause axial translation of body 16 relative to body 14. In some embodiments, expansion and/or contraction of cage 12 is facilitated by various configurations, such as, for example, mechanical, pneumatic and/or hydraulic components disposed with the surfaces of cage 12, for example, disposed within cavity 38. In some embodiments, cage 12 is configured for continuous expansion, which includes incremental expansion. In some embodiments, incremental expansion may include discrete increments of a particular linear dimension. In some embodiments, the increments of linear dimension may include a range of approximately 0.1-1.0 mm.

In operation, implant 20 is disposed in a first, collapsed orientation (not shown) such that body 14 and body 16 are disposed in a concentric configuration with longitudinal axis A1 and disposed in a telescopic arrangement for delivery and implantation adjacent a surgical site. Bodies 14, 16 are seated concentrically such that substantially all of body 16 is disposed within body 14. Endcap 22 is connected with body 14 of cage 12. Endcap 22 is rotated, in a direction shown by arrow A in FIG. 4, such that portion 90 of mating part 24 engages peg 26 of mating part 21 and at least one of member 88 and peg 26 deflects such that portion 92 and slot 32 are rotatably aligned. Peg 26 is captured between spikes 98, 100 to dispose wall 66 and cage 12 in the interlocking configuration. In the interlocking configuration, mating parts 21, 24 of cage 12 and endcap 22, respectively, are matingly engaged. Endcap 54 is matingly engaged to end 48 of body 16 of cage 12 via a similar method. In the interlocking configuration, endcaps 22, 54 are prevented from rotating such that implant 20 is steady upon insertion between vertebrae.

Cage 12 is delivered to the surgical site adjacent vertebrae V with a delivery instrument (not shown) including a driver via the protected passageway for the arthrodesis treatment. The driver delivers cage 12 into a prepared vertebral space S, between vertebra V1 and vertebra V2. Cage 12 is manipulated such that surface 72 of endcap 22 engages vertebral endplate surface E1 and surface 108 of endcap 54 engages vertebral endplate surface E2. Sides 68 of endcap 22 are aligned with opposite ends of apophyseal ring AR of vertebral body V1 and arcuate portion 76 is in nested engagement with vertebral endplate surface E1. Sides 104 of endcap 54 are aligned with opposite ends of apophyseal ring AR of vertebral body V2 and arcuate portion 112 is in nested engagement with vertebral endplate surface E2.

Body 16 is axially translated relative to body 14 for selective expansion in vivo to an expanded configuration, as shown in FIG. 5, and described herein. As such, cage 12 expands within vertebral space S. In the expanded orientation, as shown in FIG. 5, body 14 and endcap 22 are disposed to engage adjacent vertebral soft tissue and bone surfaces, as will be described, to restore height and provide support in place of removed vertebrae and/or intervertebral tissue.

Implant 20 is configured for axial expansion along axis A1. In one embodiment, implant 20 may expand in an arcuate configuration along a curvature relative to axis A1. In some embodiments, all or only a portion of implant 20 may be arcuately expanded, such as one or all of bodies 14, 16 may include a curvature relative to longitudinal axis A1.

In one embodiment, implant 20 is expanded at a selected amount of spacing and/or distraction between vertebrae such that endcap 22 engages vertebral endplate surface E1 and endcap 54 engages vertebral endplate surface E2 to restore vertebral spacing and provide distraction and/or restore mechanical support function. In one embodiment, implant 20 is expanded, as discussed herein, progressively and/or gradually to provide an implant configured to adapt to the growth of a patient including the vertebrae. In some embodiments, the height of implant 20 may also be decreased over a period of time and/or several procedures to adapt to various conditions of a patient.

In some embodiments, implant 20 provides a footprint that improves stability and decreases the risk of subsidence into tissue. In some embodiments, implant 20 provides height restoration between vertebral bodies, decompression, restoration of sagittal and/or coronal balance and/or resistance of subsidence into vertebral endplates.

In assembly, operation and use, system 10 including implant 20, similar to that described with regard to FIGS. 1-5, is employed with a surgical procedure, such as, for example, a lumbar corpectomy for treatment of a spine of a patient including vertebrae V. System 10 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including plates, rods, and bone engaging fasteners for securement of implant 20.

System 10 is employed with a lumbar corpectomy including surgical arthrodesis, such as, for example, fusion to immobilize a joint for treatment of an applicable condition or injury of an affected section of a spinal column and adjacent areas within a body. For example, vertebrae V include first vertebra V1 and second vertebra V2. A diseased and/or damaged vertebra and intervertebral discs are disposed between vertebrae V1 and V2. In some embodiments, system 10 is configured for insertion within vertebral space S to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, system 10 may be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, corpectomy is performed for treating the spine disorder. The diseased and/or damaged portion of vertebrae V, and diseased and/or damaged intervertebral discs are removed to create vertebral space S.

A preparation instrument (not shown) is employed to remove disc tissue, fluids, adjacent tissues and/or bone, and scrape and/or remove tissue from endplate surface E1 of vertebra V1 and/or endplate surface E2 of vertebra V2. Implant 20 is provided with at least one agent, similar to those described herein and as described above, to promote new bone growth and fusion to treat the affected section of vertebrae V.

Implant 20 is disposed in a first, collapsed orientation (not shown) such that body 14 and body 16 are disposed in a concentric configuration with longitudinal axis A1 and disposed in a telescopic arrangement for delivery and implantation adjacent a surgical site. Bodies 14, 16 are seated concentrically such that substantially all of body 16 is disposed within body 14. Endcap 22 is connected with body 14 of cage 12. Endcap 22 is rotated, in a direction shown by arrow A in FIG. 4, such that portion 90 of mating part 24 engages peg 26 of mating part 21 and at least one of member 88 and peg 26 deflects such that portion 92 and slot 32 are rotatably aligned. Peg 26 is captured between spikes 98, 100 to dispose wall 66 and cage 12 in the interlocking configuration. In the interlocking configuration, mating parts 21, 24 of cage 12 and endcap 22, respectively, are matingly engaged. Endcap 54 is matingly engaged to end 48 of body 16 of cage 12 via a similar method. In the interlocking configuration, endcaps 22, 54 are prevented from rotating such that implant 20 is steady upon insertion between vertebrae.

Cage 12 is delivered to the surgical site adjacent vertebrae V with a delivery instrument (not shown) including a driver via the protected passageway for the arthrodesis treatment. The driver delivers cage 12 into a prepared vertebral space S, between vertebra V1 and vertebra V2. Cage 12 is manipulated such that surface 72 of endcap 22 engages vertebral endplate surface E1 and surface 108 of endcap 54 engages vertebral endplate surface E2. Sides 68 of endcap 22 are aligned with opposite ends of apophyseal ring AR of vertebral body V1 and arcuate portion 76 is in nested engagement with vertebral endplate surface E1. Sides 104 of endcap 54 are aligned with opposite ends of apophyseal ring AR of vertebral body V2 and arcuate portion 112 is in nested engagement with vertebral endplate surface E2.

Body 16 is axially translated relative to body 14 for selective expansion in vivo to an expanded configuration, as shown in FIG. 5. As such, cage 12 expands within vertebral space S. In the expanded orientation, as shown in FIG. 5, body 14 and endcap 22 are disposed to engage adjacent vertebral soft tissue and bone surfaces, as will be described, to restore height and provide support in place of removed vertebrae and/or intervertebral tissue.

Implant 20 engages and spaces apart opposing endplate surfaces E1, E2 and is secured within vertebral space S to stabilize and immobilize portions of vertebrae V in connection with bone growth for fusion and fixation of vertebrae V1, V2. Fixation of implant 20 with endplate surfaces E1, E2 may be facilitated by the resistance provided by the joint space and/or engagement with endplate surfaces E1, E2. A lock can be provided to prevent body 16 from axially translating relative to body 14 to fix implant 20 in a selected expanded and/or contracted orientation, including those described herein.

In some embodiments, implant 20 may engage only one vertebral endplate. In some embodiments, an agent(s), as described herein, may be applied to areas of the surgical site to promote bone growth. Components of system 10 including implant 20 can be delivered or implanted as a pre-assembled device or can be assembled in situ. Components of system 10 including implant 20 may be completely or partially revised, removed or replaced in situ. In some embodiments, one or all of the components of system 10 can be delivered to the surgical site via mechanical manipulation and/or a free hand technique.

In one embodiment, implant 20 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, system 10 can be used with screws to enhance fixation. In some embodiments, system 10 and any screws and attachments may be coated with an agent, similar to those described herein, for enhanced bony fixation to a treated area. The components of system 10 can be made of radiolucent materials such as polymers. Radiomarkers may be included for identification under x-ray, fluoroscopy, CT or other imaging techniques.

In one embodiment, system 10 includes a plurality of implants 20. In some embodiments, employing a plurality of implants 20 can optimize the amount vertebral space S can be spaced apart such that the joint spacing dimension can be preselected. The plurality of implants 20 can be oriented in a side by side engagement, spaced apart and/or staggered.

In some embodiments, the use of microsurgical and image guided technologies may be employed to access, view and repair spinal deterioration or damage, with the aid of system 10. Upon completion of the procedure, the non-implanted components, surgical instruments and assemblies of system 10 are removed and the incision is closed.

Figure 7:
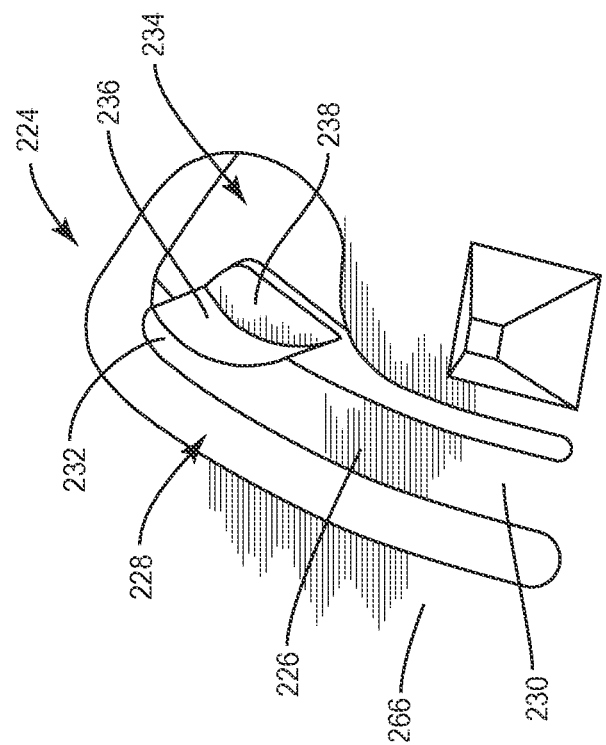
FIG. 7 is a breakaway view of the components shown in FIG. 6.
Figure 6:
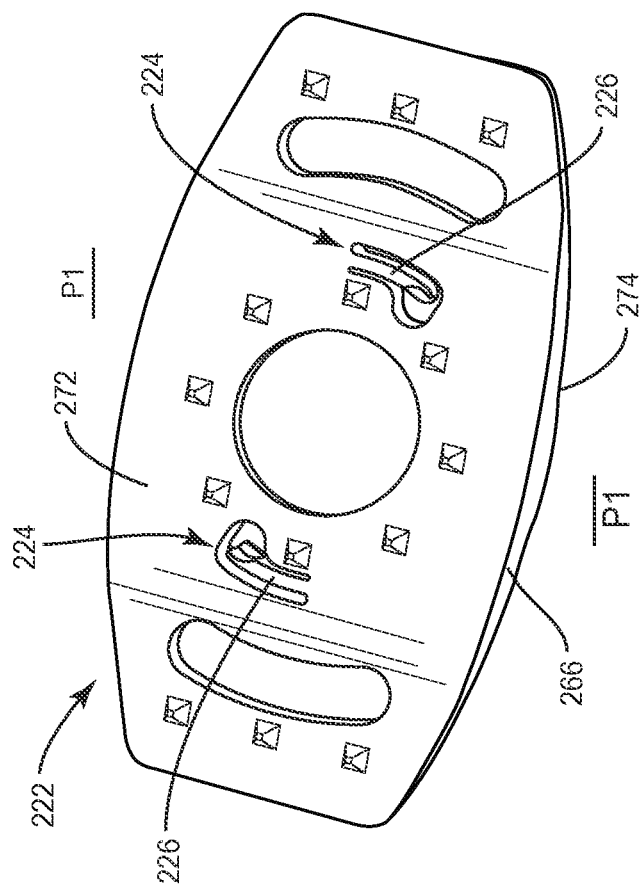
FIG. 6 is a perspective view of components of one embodiment of a spinal implant in accordance with the principles of the present disclosure.
Figure 8:
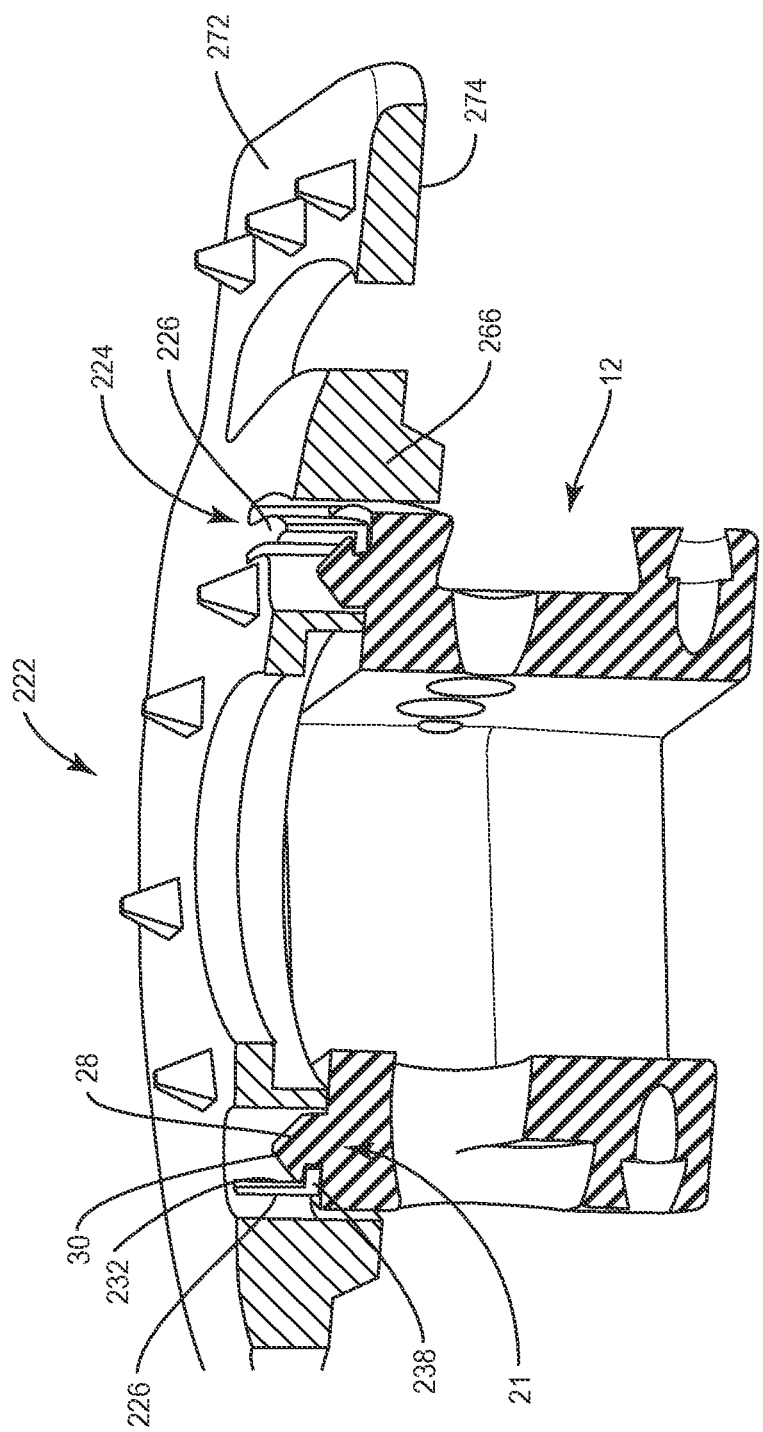
FIG. 8 is a breakaway view, in cross section, of the components shown in FIG. 6.

In one embodiment, as shown in FIGS. 6-8, system 10 includes implant 20, similar to that described above with regard to FIGS. 1-5, having an endcap 222, similar to endcaps 22 and 54 described above, and cage 12. Endcap 22 includes a wall 266 having a surface 272 configured for engagement with vertebral tissue, such as, for example, vertebral endplate surface E1 and a surface 274 configured for engagement with cage 12. Endcap 222 includes a mating part 224. Mating part 224 includes a relatively movable member, such as, for example, at least one resiliently biased finger 226 disposable with slot 32 of mating part 21 of cage 12. Finger 226 is disposed between surfaces 272, 274 of endcap 222 and extends in a plane P1 of wall 266 in an opening 228 of wall 266. Opening 228 has a P-shaped configuration. In some embodiments, opening 228 is variously shaped, such as, for example, oval, oblong, triangular, square, hexagonal, polygonal, irregular, uniform, non-uniform and/or tapered. Finger 226 has an arcuate configuration. In some embodiments, finger 226 is variously configured, such as, for example, those alternatives described herein. Finger 226 extends between an end 230 engaged to wall 266 and an end 232 disposed in an enlarged portion 234 of opening 228. End 232 includes a cutout portion 236 and a flange, such as, for example, a tab 238 configured for disposal in slot 32 of peg 26.

To connect endcap 222 with cage 12, openings 228 of endcap 222 are aligned with pegs 26 of mating part 21 of cage 12. Tab 238 is positioned into engagement with cone-shaped portion 30 of peg 26 and finger 226 deflects outwardly in plane P1. Tab 238 travels along cone-shaped portion 30 and deflects inwardly in plane P1 and into slot 32 to dispose wall 266 and cage 12 in the interlocking configuration. In some embodiments, cage 12 includes mating part 224 and endcap 222 includes mating part 21.

Figure 9:
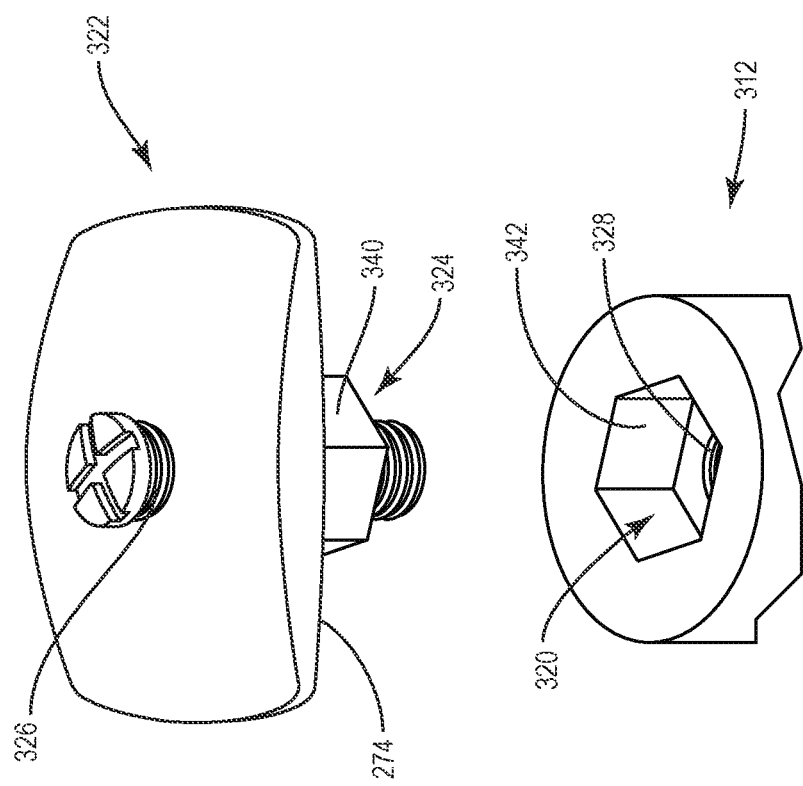
FIG. 9 is a perspective view of components of one embodiment of a spinal implant in accordance with the principles of the present disclosure with parts separated.

In one embodiment, as shown in FIG. 9, system 10 includes implant 20, similar to that described above with regard to FIGS. 1-5, having an endcap 322, similar to endcaps 22, 54 described above, and a cage 312, similar to cage 12 described above. Endcap 322 includes a mating part 324. Mating part 324 includes a relatively movable member, such as, for example, a relatively rotatable screw member 326 engageable with a threaded cavity 328 of a mating part 320 of cage 312. Mating part 324 includes a hexagonal member 340 engageable with a hexagonal inner surface 342 of mating part 320. Screw member 326 extends through hexagonal member 340 and into threaded cavity 328. Surface 274 is rotatably aligned with cage 312 such that mating parts 320, 324 are rotatably aligned.

Figure 10:
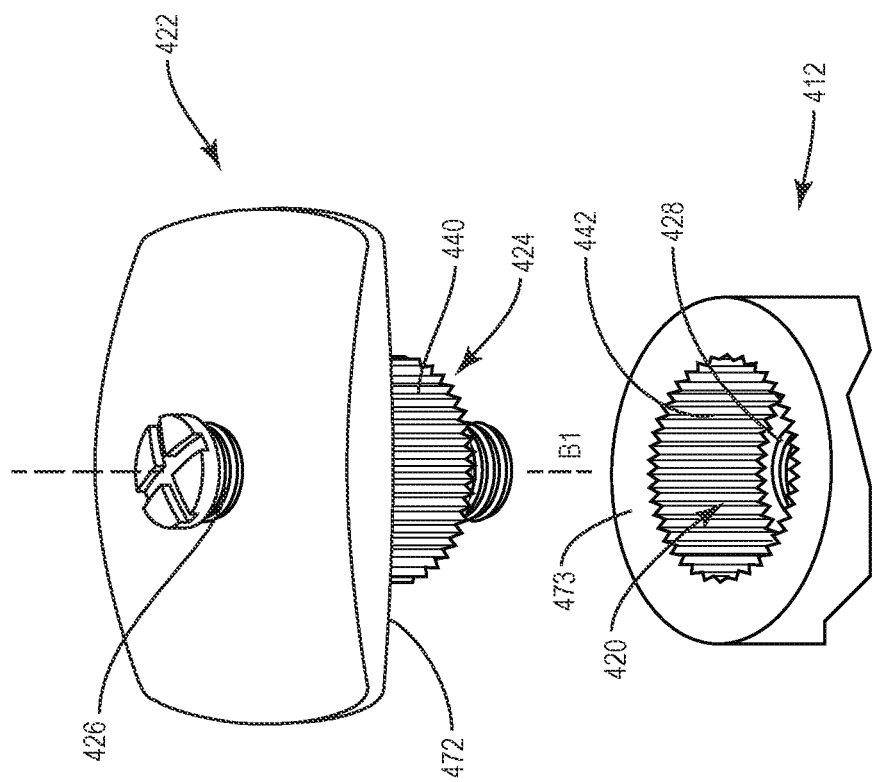
FIG. 10 is a perspective view of components of one embodiment of a spinal implant in accordance with the principles of the present disclosure with parts separated.

In one embodiment, as shown in FIG. 10, system 10 includes implant 20, similar to that described above with regard to FIGS. 1-5, having an endcap 422, similar to endcaps 22, 54 described above, and cage 412, similar to cage 12 described above. Endcap 422 includes a mating part 424. Mating part 424 includes a relatively movable member, such as, for example, a relatively rotatable screw member 426, similar to screw member 326 described above with regard to FIG. 9. Screw member 426 is engageable with a threaded cavity 428 of a mating part 420 of cage 412. Mating part 424 includes a splined outer surface 440. Individual splines of splined surface 440 are oriented substantially parallel with longitudinal axis B1. Splined surface 440 has a cylindrical configuration. Splined surface 440 is engageable with a splined inner surface 442 of mating part 420 of cage 412. Individual splines of splined surface 442 are oriented substantially parallel with longitudinal axis B1. Splined surface 442 has a cylindrical configuration configured for disposal of splined surface 440. In some embodiments, surface 472 of endcap 422 includes splines engageable with splines on a surface 473 of cage 412. In some embodiments, splined surfaces 440, 442 are variously configured, such as, for example, oval, oblong, triangular, square, hexagonal, polygonal, irregular, uniform, non-uniform and/or tapered.

Figure 11:
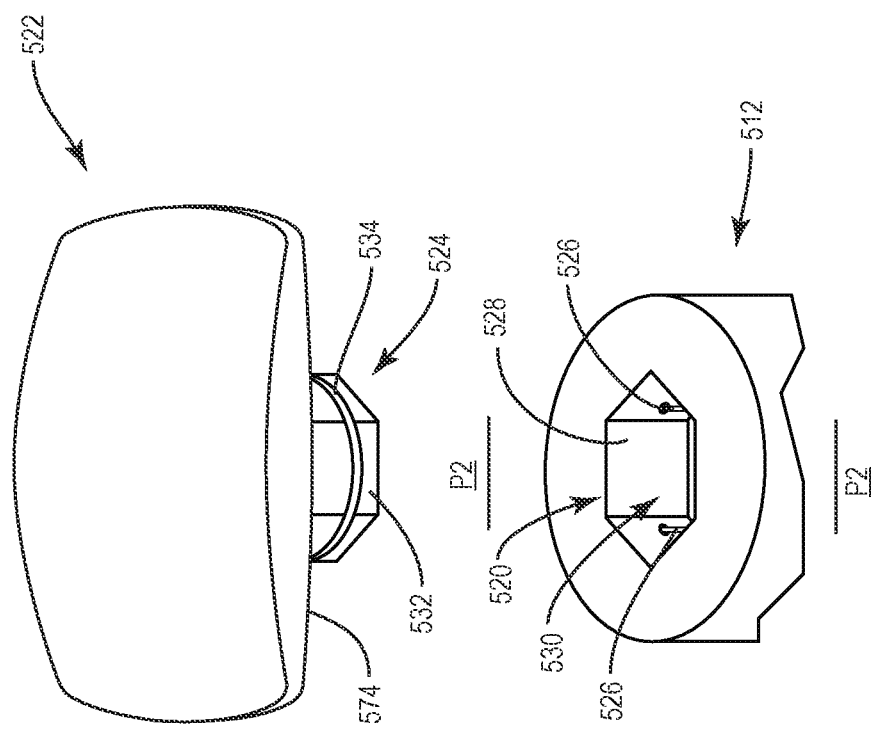
FIG. 11 is a perspective view of components of one embodiment of a spinal implant in accordance with the principles of the present disclosure with parts separated.

In one embodiment, as shown in FIG. 11, system 10 includes implant 20, similar to that described above with regard to FIGS. 1-5, having an endcap 522, similar to endcaps 22, 54 described above, and a cage 512, similar to cage 12 described above. Cage 512 includes a mating part 520, similar to mating part 320 described above with regard to FIG. 9. Mating part 520 includes a relatively movable member, such as, for example, Nitinol wires 526 extending in cross-sectional plane P2 of cage 512. Nitinol wires 526 have a substantially parallel orientation relative to one another and are disposed on opposite ends of an inner surface 528 of mating part 520. Inner surface 528 defines a cavity 530 having a hexagonal cross section configuration configured for disposal of a correspondingly shaped outer surface 532 of a mating part 524 of endcap 522. Mating part 524 includes a circumferential recess 534 configured for disposal of Nitinol wires 526. Outer surface 532 has a hexagonal configuration such that inner and outer surfaces 528, 532 are matingly engageable. In some embodiments, surfaces 528, 532 are variously configured, such as, for example, those alternatives herein described. In some embodiments, recess 534 is a pair of recesses disposed in opposite ends of outer surface 532. To engage endcap 522 with cage 512, a surface 574 of endcap 522 and cage 512 are rotatably aligned and outer surface 532 is positioned within cavity 530. Nitinol wires 526 deflect outwardly away from one another during insertion of mating part 524 into cavity 530. Upon insertion of mating part 524 into cavity 530, Nitinol wires 526 deflect inwardly towards one another into recess 534 to capture endcap 522 in cavity 530.

Figure 12:
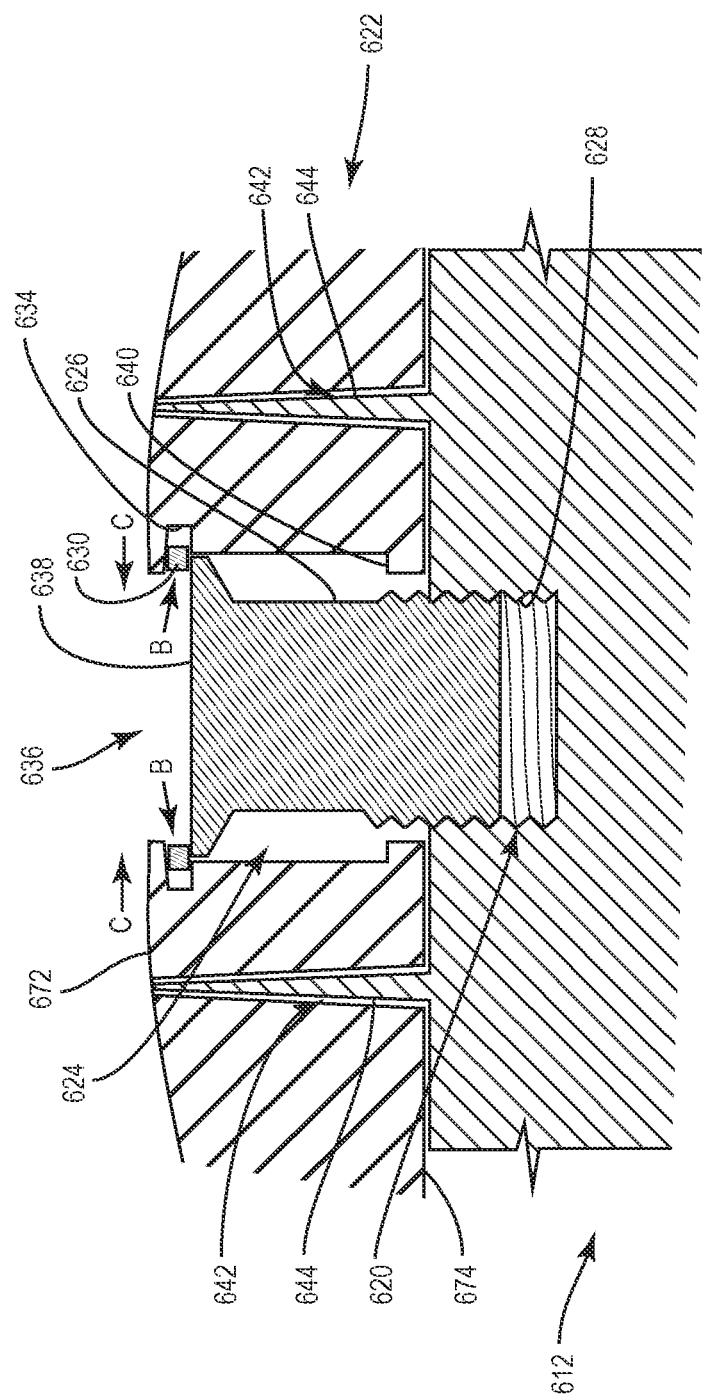
FIG. 12 is a breakaway cross sectional view of components of one embodiment of a spinal implant in accordance with the principles of the present disclosure.

In one embodiment, as shown in FIG. 12, system 10 includes implant 20, similar to that described above with regard to FIGS. 1-5, having an endcap 622, similar to endcaps 22, 54 described above, and a cage 612, similar to cage 12 described above. Endcap includes surfaces 672, 674, similar to surfaces 72, 74 described above with regard to FIGS. 1-5. Endcap 622 includes a passageway 636 extending between surfaces 672, 674. Endcap 622 includes a biasing member, such as, for example, an annular member 630 disposable in an annular notch 634 of endcap 622. Endcap 622 includes protrusions 640 extending into passageway 636. Endcap 622 includes a mating part 624. Mating part 624 includes a relatively movable member, such as, for example, a rotatable screw member 626, similar to screw members 326, 426 described above with regard to FIGS. 9-10. Screw member 626 includes a screw head 638. Screw member 626 is disposable in passageway 636 and with a threaded inner cavity 628 of a mating part 620 of cage 612.

To connect endcap 622 with cage 612, screw member 626 is rotated such that screw member 626 axially translates through passageway 636. Screw member 626 overcomes the resilient bias of annular member 630 such that annular member 630 deflects and/or deforms about head 638 of screw member 626, in the direction shown by arrow B in FIG. 12. Annular member 630 expands such that screw member 626 passes through passageway 636 of endcap 622. Upon seating of screw head 638 with protrusions 640 of endcap 622, annular member 630 is resiliently biased and collapses, in the direction shown by arrow C in FIG. 12, to resist and/or prevent movement of screw member 626 back out of passageway 636. Endcap 622 includes a plurality of circumferentially disposed channels 642 that extend between surfaces 672, 674 of endcap 622. Cage 612 includes a plurality of circumferentially disposed spikes 644 disposable with channels 642 such that relative rotation of endcap 622 and cage 12 is resisted.

Figure 13:
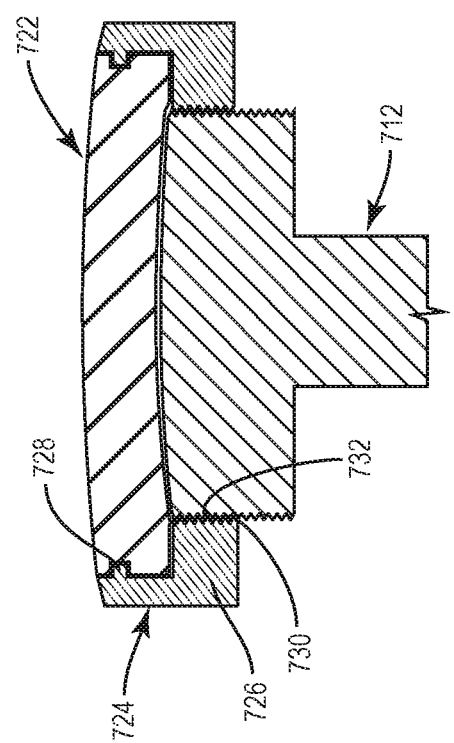
FIG. 13 is a side breakaway view of components of one embodiment of a spinal implant in accordance with the principles of the present disclosure.

In one embodiment, as shown in FIG. 13, system 10 includes implant 20, similar to that described above with regard to FIGS. 1-5, having an endcap 722, similar to endcaps 22, 54 described above, and a cage 712, similar to cage 12 described above. Endcap 722 includes a mating part 724. Mating part 724 includes a relatively movable member, such as, for example, a circumferential ring 726. Ring 726 includes a flange 728 engageable with endcap 722. Ring 726 includes a threaded inner surface 730 threaded with a threaded outer surface 732 of mating part 720 of cage 712 such that the rotation of ring 726 matingly engages endcap 722 and cage 712.

Figure 14:
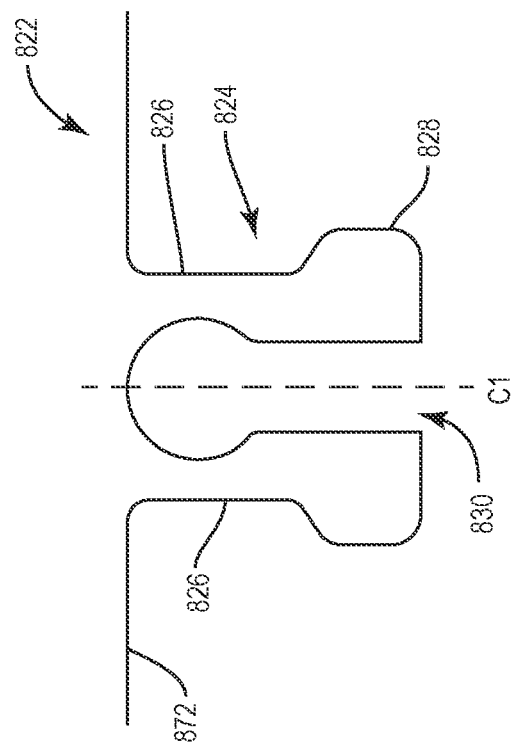
FIG. 14 is a side view of components of one embodiment of a spinal implant in accordance with the principles of the present disclosure.

In one embodiment, as shown in FIG. 14, system 10 includes implant 20, similar to that described above with regard to FIGS. 1-5, having a endcap 822, similar to endcaps 22, 54 described above, and a cage (not shown), similar to cage 12 described above. Endcap 822 includes a mating part 824, similar to mating part 24 described above. Mating part 824 includes a relatively movable member, such as, for example, a pair of arms 826 extending from surface 872 of endcap 822 and being substantially parallel with a longitudinal axis C1. Arms 826 include a rounded end 828 configured for disposal in a correspondingly shaped inner surface of the cage (not shown). Arms 826 define a cavity 830 having a keyhole configuration such that arms 826 are moveable. In some embodiments, cavity 830 is variously configured, such as, for example, those alternatives herein described. To connect endcap 822 with the cage, arms 826 are positioned into contact with the mating part of the cage such that arms 826 deflect inward. Endcap 822 is translated within the cage and arms 826 deflect outward such that rounded end 828 engages the correspondingly shaped inner surface of the cage to interlock the cage and endcap 822.

Figure 15:
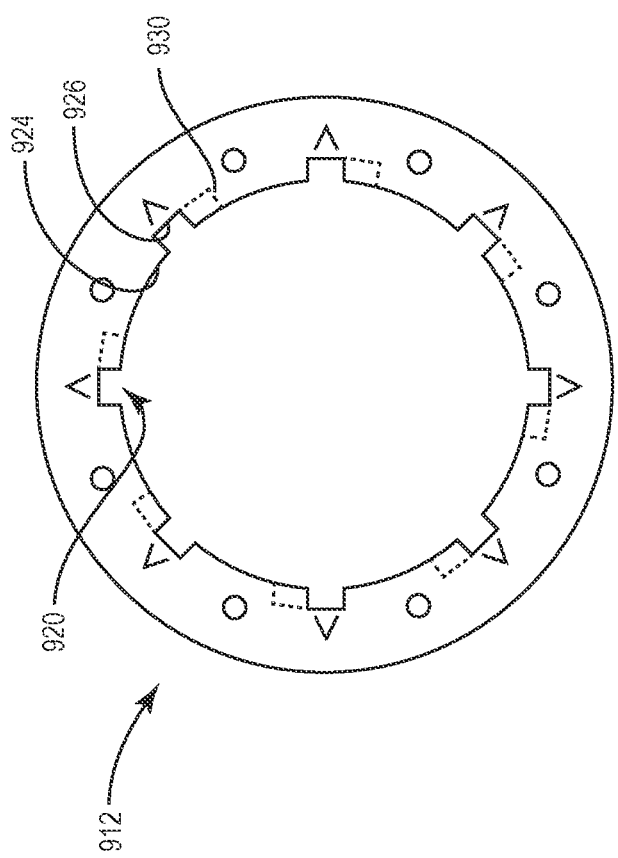
FIG. 15 is a top view, in part phantom, of components of one embodiment of a spinal implant in accordance with the principles of the present disclosure.

In one embodiment, as shown in FIG. 15, system 10 includes implant 20, similar to that described above with regard to FIGS. 1-5, having an endcap (not shown), similar to endcaps 22, 54 described above, and a cage 912, similar to cage 12 described above. The endcap includes a mating part (not shown) having a cog-shaped configuration configured for mating engagement with a mating part 920 of cage 912. Mating part 920 includes an inner surface 924 having a cog-shaped cross section configuration. Inner surface 924 includes a series of annularly disposed recesses 926 corresponding to teeth (not shown) of the cog-shaped mating part of the endcap. Mating part 920 includes a plurality of undercuts 930, shown in phantom in FIG. 15, which intersect recesses 926 such that rotation of endcap and/or cage 912 orients the teeth of the mating part out of recesses 926 and into undercuts 930 to interlock the mating parts of cage 912 and the endcap.

Figure 16:
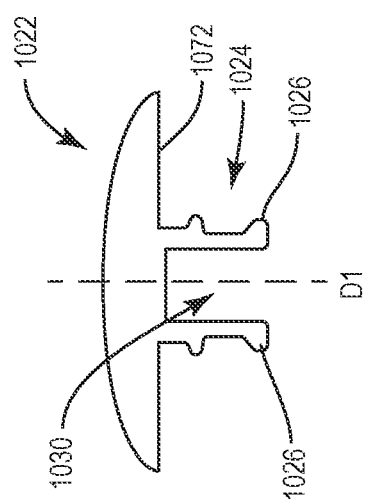
FIG. 16 is a side view of components of one embodiment of a spinal implant in accordance with the principles of the present disclosure.

In one embodiment, as shown in FIG. 16, system 10 includes implant 20, similar to that described above with regard to FIGS. 1-5, having an endcap 1022, similar to endcaps 22, 54 described above, and a cage (not shown), similar to cage 12 described above. Endcap 1022 includes a mating part 1024. Mating part 1024 includes a relatively movable member, such as, for example, a pair of arms 1026 extending from surface 1072 of endcap 1022 and being substantially parallel with a longitudinal axis D1. Arms 1026 are configured for disposal in a correspondingly shaped inner surface of the cage (not shown). Arms 1026 define a cavity 1030 such that arms 1026 are moveable. To connect endcap 1022 with the cage, arms 1026 are positioned into contact with a mating part of the cage such that arms 1026 deflect inward. Endcap 1022 is translated within the cage and arms 1026 deflect outward such that arms 1026 engage the correspondingly shaped mating part of the cage.

In one embodiment, as shown in FIG. 17, system 10 includes implant 20, similar to that described above with regard to FIGS. 1-5, having an endcap 1122, similar to endcaps 22, 54 described above, and a cage 1112, similar to cage 12 described above. Endcap 1122 includes a mating part 1124. Mating part 1124 includes a relatively movable member, such as, for example, a plurality of circumferentially disposed pairs of legs 1126. Each pair of legs 1126 extend between an end 1128 connected to surface 1172 and an end 1130 including a flange 1132. Flanges 1132 on each leg are oriented outwardly from one another. Legs 1126 are disposable with a plurality of circumferentially disposed channels 1134, shown in phantom, in cage 1112. To connect endcap 1122 with cage 1112, each pair of legs 1126 are positioned within a channel 1134 such that legs 1126 deflect inwardly towards one another. Upon translation of legs 1126 through channels 1134, legs 1126 deflect outwardly away from one another and flanges 1132 engage an underside 1136 of cage 1112 such that endcap 1122 and cage 1112 are matingly engaged.

In one embodiment, as shown in FIG. 18, system 10 includes implant 20, similar to that described above with regard to FIGS. 1-5, having an endcap 1222, similar to endcaps 22, 54 described above, and a cage 1212, shown in phantom, similar to cage 12 described above. Endcap 1222 includes a mating part 1224. Mating part 1224 includes a relatively movable member, such as, for example, a rotatable cam lock 1226 and a pair of pivotable arms 1228. Arms 1228 extend between an end 1230 pivotally engageable with a surface 1274 of endcap 1222 and an end 1232 having a notch 1234. A mating part 1220 of cage 1212 includes a projection 1236 configured for disposal in notch 1234 of arms 1228. Rotation of cam lock 1226 causes cam lock 1226 to engage arms 1228 such that arms 1228 pivot about end 1230 such that projection 1236 engages notch 1234 to interlock endcap 1222 and cage 1212. In some embodiments, projection 1236 and notch 1234 are variously configured, such as, for example, oval, oblong, triangular, rectangular, square, polygonal, irregular, uniform, non-uniform, variable and/or tapered.

Figure 20:
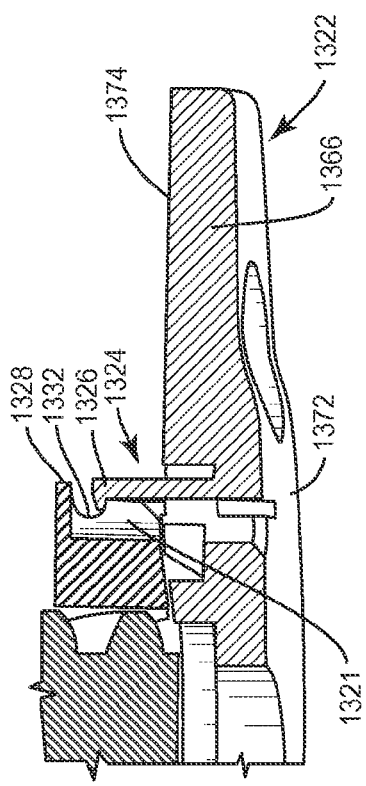
FIG. 20 is an enlarged view of detail A shown in FIG. 19.
Figure 19:
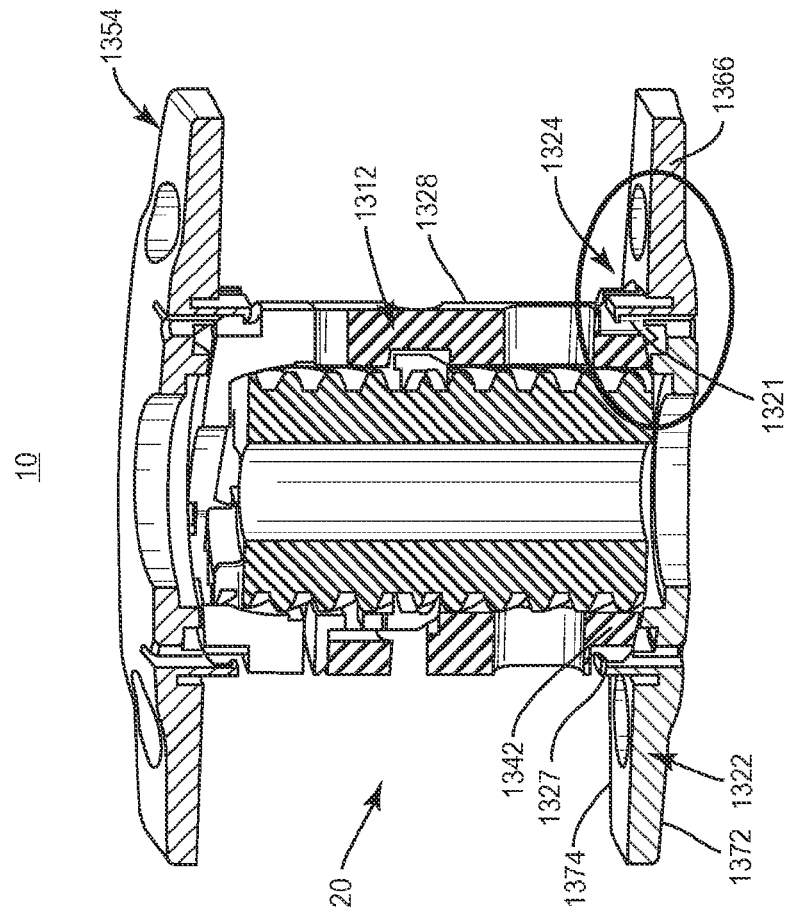
FIG. 19 is a perspective view, in cross section, of components of one embodiment of a spinal implant in accordance with the principles of the present disclosure.

In one embodiment, as shown in FIGS. 19 and 20, system 10 includes implant 20, similar to that described above with regard to FIGS. 1-5, having endcaps 1322, 1354, similar to endcaps 22 and 54 described herein, and a cage 1312, similar to cage 12 described herein. Endcap 1322 includes a wall 1366 having a surface 1372 configured for engagement with vertebral tissue and a surface 1374 configured for engagement with cage 1312. Endcap 1322 includes a mating part 1324. Mating part 1324 includes a relatively movable member, such as, for example, at least two resiliently biased latches 1326, 1327 disposable with a mating part 1321 of cage 12. Latches 1326, 1327 extend from surface 1374 of cage 1312. Mating part 1321 includes at least two notches, such as, for example, indentations 1332 in an outer surface 1328 of cage 1312 each configured for disposal of latches 1326, 1327. Latches 1326, 1327 engage indentations 1332 in a snap fit engagement such that endcap 1322 and cage 1312 are connected. In one embodiment, at least an end 1342 of cage 1312 has a hexagonal-shaped cross section configuration, countersink feature, or any of the configurations described herein, such that relative rotation of endcap 1322 and cage 1312 is resisted and/or prevented. In some embodiments, end 1342 has various cross section configurations, such as, for example, those alternatives described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An interbody endcap comprising:
a wall having a first surface connected to an interbody implant and a second surface including an arcuate portion configured for engagement with a vertebral endplate surface when the interbody endcap and a second endcap that is coupled to the interbody implant are each in contact with vertebral endplate surfaces, the wall having an opening that extends through the first and second surfaces and a first mating part positioned within the opening that is configured to engage a second mating part of the interbody implant,
wherein the second surface extends outwardly from the interbody implant to at least adjacent a perimeter of the vertebral endplate surface.

2. An interbody endcap as recited in claim 1, wherein the second surface extends to an apophyseal ring of the vertebral endplate surface.

3. An interbody endcap as recited in claim 1, wherein the first surface is connected to the interbody implant via rotational interlocking of the mating parts.

4. An interbody endcap as recited in claim 1, wherein the second surface extends between a first end and a second end such that the arcuate portion is disposed between the ends.

5. An interbody endcap as recited in claim 4, wherein the ends each include a substantially planar configuration.

6. An interbody endcap as recited in claim 1, wherein the arcuate portion is disposed in a nested engagement with the vertebral endplate surface.

7. An interbody endcap as recited in claim 1, wherein the wall includes a rectangular configuration.

8. An interbody endcap as recited in claim 7, wherein the rectangular wall includes a pair of short sides and a pair of long sides, the short sides extending to at least adjacent the perimeter of the vertebral endplate surface.

9. An interbody endcap as recited in claim 1, wherein the wall has a non-uniform thickness defined between the first and second surfaces.

10. An interbody endcap comprising:
a wall having a first surface including a first mating part disposed for engagement with a second mating part of an interbody implant such that the first surface is aligned with the interbody implant such that the wall is disposable in an interlocking configuration with the interbody implant, wherein at least one of the mating parts includes a relatively movable member that is engageable with the other of the mating parts to dispose the wall and the interbody implant in the interlocking configuration, the wall further having a second surface configured for engagement with a vertebral endplate surface, and wherein the first mating part includes a plurality of resiliently biased members that are rotatably aligned with a plurality of circumferentially disposed slots of the second mating part for disposal of the wall and the implant in the interlocking configuration.

11. A spinal implant comprising:

an interbody implant extending between a first end and a second end;

a first interbody endcap coupled to the first end having a first surface including a first mating part disposed for engagement with a second mating part of the first end of the interbody implant such that the first surface is aligned with the interbody implant such that the first interbody endcap is disposable in an interlocking configuration with the interbody implant, wherein at least one of the mating parts includes a relatively movable member that is engageable with the other of the mating parts to dispose the first interbody endcap and the interbody implant in the interlocking configuration, the first interbody endcap further including a second surface including an arcuate portion configured for engagement with a first vertebral endplate surface when the first interbody endcap and a second endcap that is coupled to the second end of the interbody implant are each in contact with vertebral endplates, wherein the second surface extends outwardly from the interbody implant to at least adjacent a perimeter of the first vertebral endplate surface and the first mating part is positioned within an opening that extends through the first and second surfaces; and a second interbody endcap having a first surface connected to the second end of the interbody implant and a second surface including an arcuate portion configured for engagement with a second vertebral endplate surface, wherein the second surface extends outwardly from the interbody implant to at least adjacent a perimeter of the second vertebral endplate surface.

12. An interbody endcap as recited in claim 1, wherein the first mating part includes a plurality of resiliently biased members that are rotatably aligned with a plurality of circumferentially disposed slots of the second mating part for disposal of the wall and the implant in an interlocking configuration.

13. An interbody endcap as recited in claim 1, wherein the first mating part includes a plurality of resiliently biased members and the second mating part comprises a plurality of slots that engage the members for disposal of the wall and the implant in an interlocking configuration.

14. An interbody endcap as recited in claim 13, wherein the members are spaced apart from one another.

15. An interbody endcap as recited in claim 1, wherein the first mating part comprises a cutout portion and a tab, the tab being configured for disposal in a slot in the second mating part.

16. An interbody endcap as recited in claim 1, wherein the first mating part is resiliently biased and comprises a cutout portion and a tab, the tab being configured to deflect relative to the second mating part to dispose the tab in a slot in the second mating part.

17. An interbody endcap as recited in claim 1, wherein the opening has a P-shaped configuration.

18. A spinal implant comprising:

the interbody endcap recited in claim 1; and the interbody implant, wherein the interbody implant comprises opposite top and bottom surfaces, the second mating part extending from the top surface.

19. A spinal implant as recited in claim 11, wherein the first mating part includes a plurality of resiliently biased members that are rotatably aligned with a plurality of circumferentially disposed slots of the second mating part for disposal of the wall and the implant in an interlocking configuration.

20. A spinal implant as recited in claim 11, wherein the first mating part includes a plurality of resiliently biased members and the second mating part comprises a plurality of slots that engage the members for disposal of the wall and the implant in an interlocking configuration.

* * * * *